(12) United States Patent
Harima et al.

(10) Patent No.: US 7,110,887 B2
(45) Date of Patent: Sep. 19, 2006

(54) RESIDUAL CHLORINE METER

(75) Inventors: Shinichi Harima, Fujimi (JP); Kiyoshi Sagawa, Tokyo (JP)

(73) Assignee: Tanita Corporation, Tokyo (JP)

(*) Notice: Subject to any disclaimer, the term of this patent is extended or adjusted under 35 U.S.C. 154(b) by 66 days.

(21) Appl. No.: 10/968,165

(22) Filed: Oct. 20, 2004

(65) Prior Publication Data

US 2005/0103626 A1    May 19, 2005

(30) Foreign Application Priority Data

Oct. 22, 2003  (JP) ............... 2003-361539

(51) Int. Cl.
*G01N 31/00* (2006.01)
(52) U.S. Cl. ............... 702/23; 702/22; 204/431
(58) Field of Classification Search ................. 702/23, 702/22; 204/431
See application file for complete search history.

(56) References Cited

U.S. PATENT DOCUMENTS

| | | | |
|---|---|---|---|
| 3,959,087 A * | 5/1976 | Morrow ............... | 205/778.5 |
| 4,956,063 A * | 9/1990 | Hale ............... | 205/783 |
| 5,842,150 A | 11/1998 | Renberg et al. | |
| 2002/0042686 A1 | 4/2002 | Kobayashi et al. | |

FOREIGN PATENT DOCUMENTS

| | | |
|---|---|---|
| GB | 2 319 614 A | 5/1998 |
| JP | 06-242071 | 9/1994 |
| JP | 09288083 A * | 11/1997 |
| JP | 09-32957 | 12/1997 |
| JP | 9-329577 | 12/1997 |
| JP | 2003-215119 | 7/2003 |
| WO | WO 97/42497 | 11/1997 |
| WO | WO 99/30142 | 8/1999 |

OTHER PUBLICATIONS

European Patent Office, Office Action for Application No. 04022835-5-2204-, dated Feb. 4, 2005.

* cited by examiner

*Primary Examiner*—Marc S. Hoff
*Assistant Examiner*—Janet L Suglo
(74) *Attorney, Agent, or Firm*—McDermott Will & Emery LLP

(57) ABSTRACT

A residual chlorine meter detects a pre-calibration residual chlorine reaction amount of sample water in a detection section, inputs a calibration standard residual chlorine standard concentration of the sample water in an input section, determines calibration factors from data for computing the calibration factors based on the amount and the concentration stored in a calibration factor computation data storage section in a calibration factor computation section, and stores the calibration factors in a calibration factor storage section. Then, the meter detects an on-measurement residual chlorine reaction amount of the sample water in the detection section and determines a post-calibration residual chlorine concentration of the sample water from data for computing the post-calibration residual chlorine concentration based on the on-measurement residual chlorine reaction amount and the calibration factor stored in a residual chlorine concentration computation data storage section in a residual chlorine concentration computation section.

3 Claims, 14 Drawing Sheets

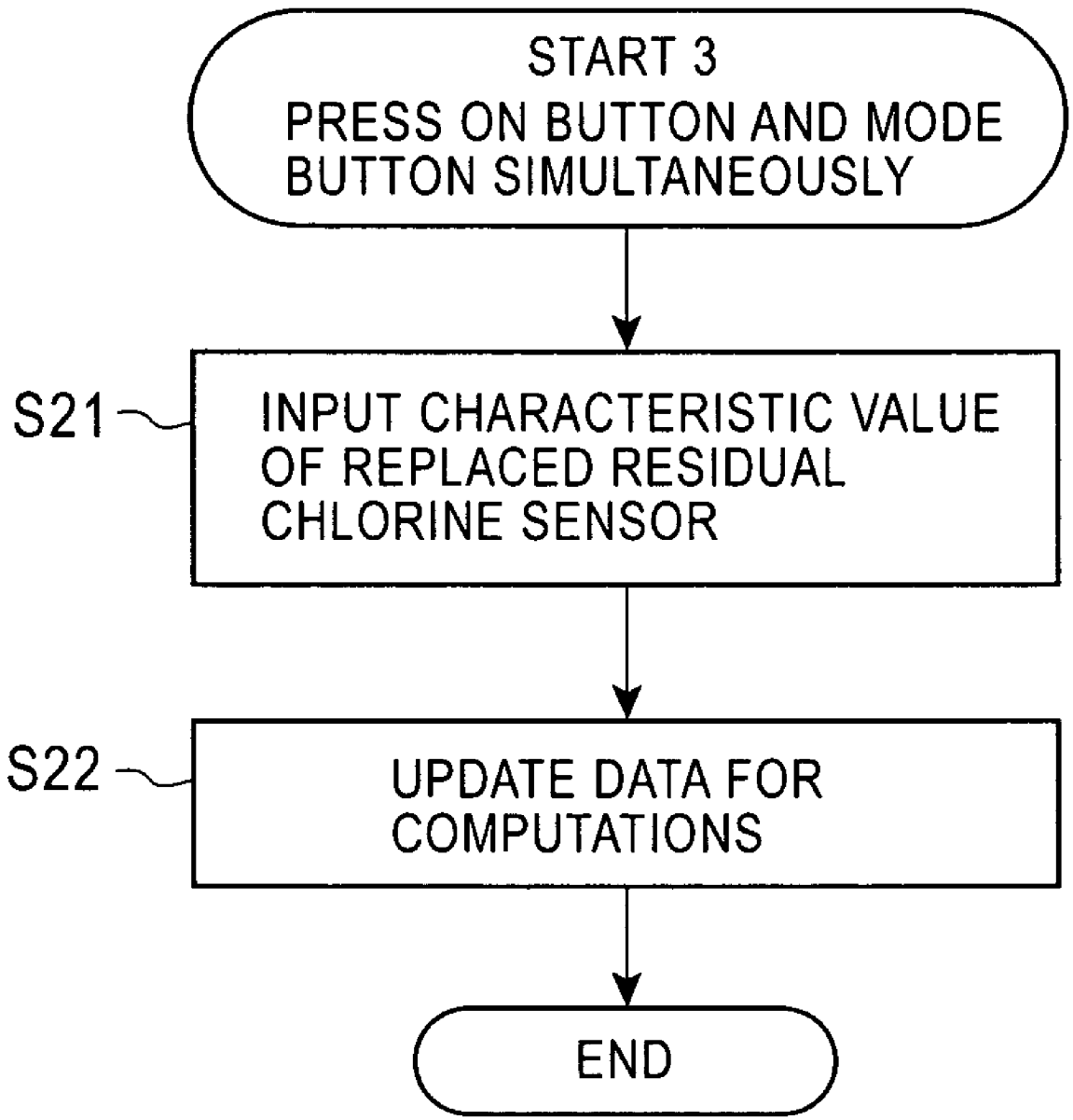

FIG. 11

| RESIDUAL CHLORINE CONCENTRATION | RESIDUAL CHLORINE REACTION AMOUNT |
|---|---|
| 0.05 | 130 |
| 0.10 | 240 (PRE-CALIBRATION SELECTED STANDARD) |
| 0.15 | 300 |
| 0.20 | 350 |
| 0.25 | 385 |
| 0.30 | 420 |
| 0.35 | 450 |
| 0.40 | 480 |
| 0.50 | 490 |
| ⋮ | ⋮ |

RESIDUAL CHLORINE METER

BACKGROUND OF THE INVENTION (i) Field of the Invention

The present invention relates to a residual chlorine meter which can measure a residual chlorine concentration in water such as tap water, water for a pool or industrial water easily.

(ii) Description of the Related Art

Water such as tap water, water for a pool or industrial water is chlorinated for the sake of sanitation. To keep a residual chlorine concentration resulting from the chlorination at an appropriate level, means for measuring the residual chlorine concentration has been disclosed.

For instance, a residual chlorine concentration measuring device disclosed in Patent Publication 1 comprises pH measuring means (pH meter) and electric conductivity measuring means (electric conductivity meter) and determines calibration factors corresponding to the measured pH and electric conductivity of sample water based on calibration curves associated with the pH dependency and electric conductivity dependency of an apparent residual chlorine concentration resulting from normalization of a true value of a residual chlorine concentration and calibrates the apparent residual chlorine concentration of the sample water based on the calibration factors so as to determine a true residual chlorine concentration. The device is means for measuring a residual chlorine concentration with excellent measurement accuracy.

Meanwhile, a residual chlorine concentration measuring method disclosed in Patent Publication 2 is a method using a phosphate buffer having a more alkaline pH than 6.5 together with a liquid DPD reagent. The method is capable of measuring a residual chlorine concentration without any problem.

Japanese Patent Laid-Open Publication No. 9-329577
Japanese Patent Laid-Open Publication No. 2003-215119

However, the residual chlorine concentration measuring device disclosed in Patent Publication 1 has a problem that since the device has generally expensive measuring means including the pH meter and the electric conductivity meter, the device as a whole becomes expensive accordingly. Meanwhile, the residual chlorine concentration measuring method disclosed in Patent Publication 2 has a problem that it requires a high running cost and is troublesome to use since it uses a liquid DPD reagent for every measurement.

Thus, in view of such conventional problems, an object of the present invention is to provide a residual chlorine meter capable of measuring a residual chlorine concentration inexpensively and easily.

SUMMARY OF THE INVENTION

A residual chlorine meter of the present invention comprises:
a detection section,
an input section,
a calibration factor computation data storage section,
a calibration factor computation section,
a calibration factor storage section,
a residual chlorine concentration computation data storage section, and
a residual chlorine concentration computation section,
wherein the detection section detects the pre-calibration residual chlorine reaction amount and on-measurement residual chlorine reaction amount of sample water,
the input section inputs the calibration standard residual chlorine concentration of the sample water,
the calibration factor computation data storage section stores in advance data for computing calibration factors based on the pre-calibration residual chlorine reaction amount and calibration standard residual chlorine concentration of the sample water,
the calibration factor computation section computes the calibration factors based on the pre-calibration residual chlorine reaction amount detected by the detection section,
the calibration standard residual chlorine concentration input by the input section, and the data stored in advance in the calibration factor computation data storage section,
the calibration factor storage section stores the calibration factors computed by the calibration factor computation section,
the residual chlorine concentration computation data storage section stores in advance data for computing the post-calibration residual chlorine concentration of the sample water based on the on-measurement residual chlorine reaction amount of the sample water and the calibration factor, and
the residual chlorine concentration computation section computes the post-calibration residual chlorine concentration of the sample water based on the on-measurement residual chlorine reaction amount detected by the detection section,
the calibration factor stored in the calibration factor storage section, and the data stored in advance in the residual chlorine concentration computation data storage section.

Further, the input section further inputs a characteristic value representing the characteristic of a residual chlorine sensor, and the residual chlorine meter further comprises a calibration factor computation data update control section which updates the data stored in the calibration factor computation data storage section based on the characteristic value input by the input section.

Further, a residual chlorine meter of the present invention comprises:
a detection section,
a calibration factor computation data storage section,
a calibration factor computation section,
a calibration factor storage section,
a residual chlorine concentration computation data storage section, and
a residual chlorine concentration computation section,
wherein the detection section detects the pre-calibration residual chlorine reaction amount and on-measurement residual chlorine reaction amount of sample water,
the calibration factor computation data storage section stores in advance data for computing calibration factors based on the pre-calibration residual chlorine reaction amount and calibration standard residual chlorine concentration of the sample water,
the calibration factor computation section computes the calibration factors based on the pre-calibration residual chlorine reaction amount detected by the detection section and the data stored in advance in the calibration factor computation data storage section,
the calibration factor storage section stores the calibration factors computed by the calibration factor computation section, the residual chlorine concentration computation data storage section stores in advance data for computing the post-calibration residual chlorine concentration of the sample water based on the on-measurement residual chlorine reaction amount of the sample water and the calibration factor, and the residual chlorine concentration computation section computes the post-calibration residual chlorine concentration of the sample water based on the on-measurement residual chlorine reaction amount detected by the detection section, the calibration factor stored in the calibration factor storage section, and the data stored in advance in the residual chlorine concentration computation data storage section.

Further, the residual chlorine meter further comprises:

an input section, and a calibration factor computation data update control section, wherein the input section inputs a characteristic value representing the characteristic of a residual chlorine sensor, and the calibration factor computation data update control section updates the data stored in the calibration factor computation data storage section based on the characteristic value input by the input section.

Further, the calibration factor computation data storage section includes a plurality of calibration factor computing equations based on a selected standard residual chlorine concentration, in the data for computing calibration factors, the calibration factor computation section computes a plurality of calibration factors based on the selected standard residual chlorine concentration, based on the calibration factor computing equations, the calibration factor storage section stores the calibration factors, the residual chlorine concentration computation data storage section includes a plurality of post-calibration residual chlorine concentration computing equations based on the selected standard residual chlorine concentration, in the data for computing the post-calibration residual chlorine concentration of sample water, and the residual chlorine concentration computation section selects one of the post-calibration residual chlorine concentration computing equations to compute the post-calibration residual chlorine concentration of the sample water.

The residual chlorine meter of the present invention, as a preparatory stage for measurements, detects the residual chlorine reaction amount of sample water at a site to be inspected in the detection section, determines calibration factors for the sample water at the site to be inspected from data for computing the calibration factors based on the residual chlorine reaction amount and residual chlorine standard concentration of the sample water stored in the calibration factor computation data storage section in the calibration factor computation section, and stores the calibration factors in the storage section. Then, as a measurement stage, the residual chlorine meter detects the residual chlorine reaction amount of the sample water at the site to be inspected in the detection section and determines the residual chlorine concentration of the sample water at the site to be inspected from data for computing the post-calibration residual chlorine concentration of the sample water based on the on-measurement residual chlorine reaction amount of the sample water and the calibration factor stored in a residual chlorine concentration computation data storage section in a residual chlorine concentration computation section. Therefore, influences by the pH and electric conductivity of sample water can be eliminated without need for use of expensive measuring means and calibration for each measurement.

Further, in the input section, a characteristic value representing the characteristic of the sensor is input, and in the calibration factor computation data update control section, the data stored in the calibration factor computation data storage section is updated. Therefore, the device can still be used without lowering accuracy even after the sensor is replaced due to a failure or some other reason.

Further, in the residual chlorine concentration computation section, one of post-calibration residual chlorine concentration computing equations based on a selected standard residual chlorine concentration is selected, and the post-calibration residual chlorine concentration of the sample water is computed. Therefore, a post-calibration residual chlorine concentration from which influences by the pH and electric conductivity of sample water have been eliminated can be determined more accurately.

BRIEF DESCRIPTION OF THE DRAWINGS

FIG. 7 is a flowchart in the replacement mode of the residual chlorine meter (Embodiments 1 and 2).

FIG. 11 is a standard table showing the relationship between the residual chlorine concentration and the residual chlorine reaction amount (Embodiment 1).

DETAILED DESCRIPTION OF THE PREFERRED EMBODIMENTS

The present inventor has paid attention to a fact that a user of a residual chlorine meter often measures sample water at the same site and a fact that changes in pH and electric conductivity which are highly influential to measurement of residual chlorine concentration are small in sample water at the same site. The present inventor has conceived such constitutions as described in the following Embodiments and achieved the present invention as a residual chlorine meter capable of measuring a residual chlorine concentration inexpensively and easily.

[Embodiment]1

Figure 1:
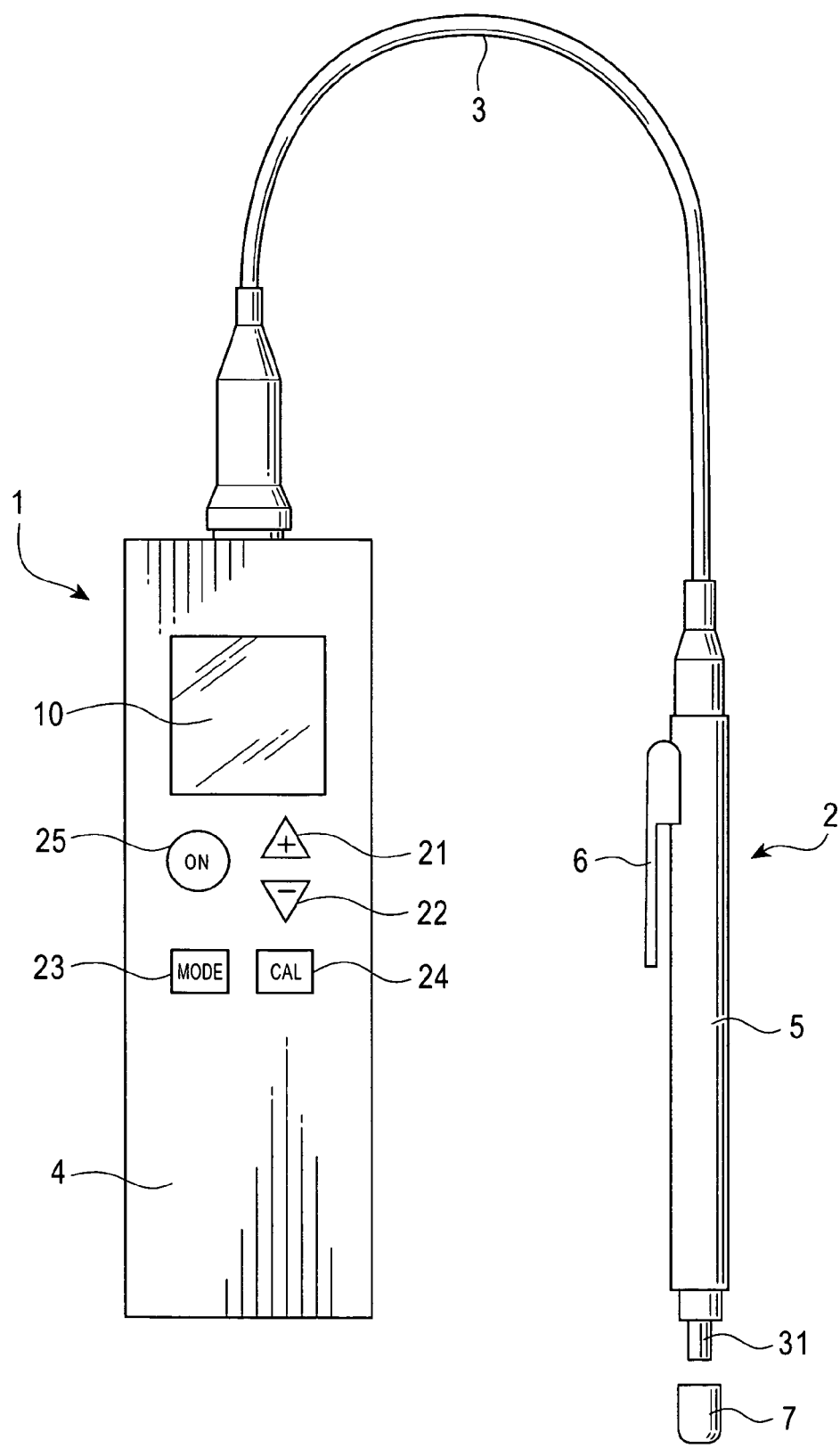
FIG. 1 is an external view of a residual chlorine meter (Embodiments 1 and 2).
Figure 2:
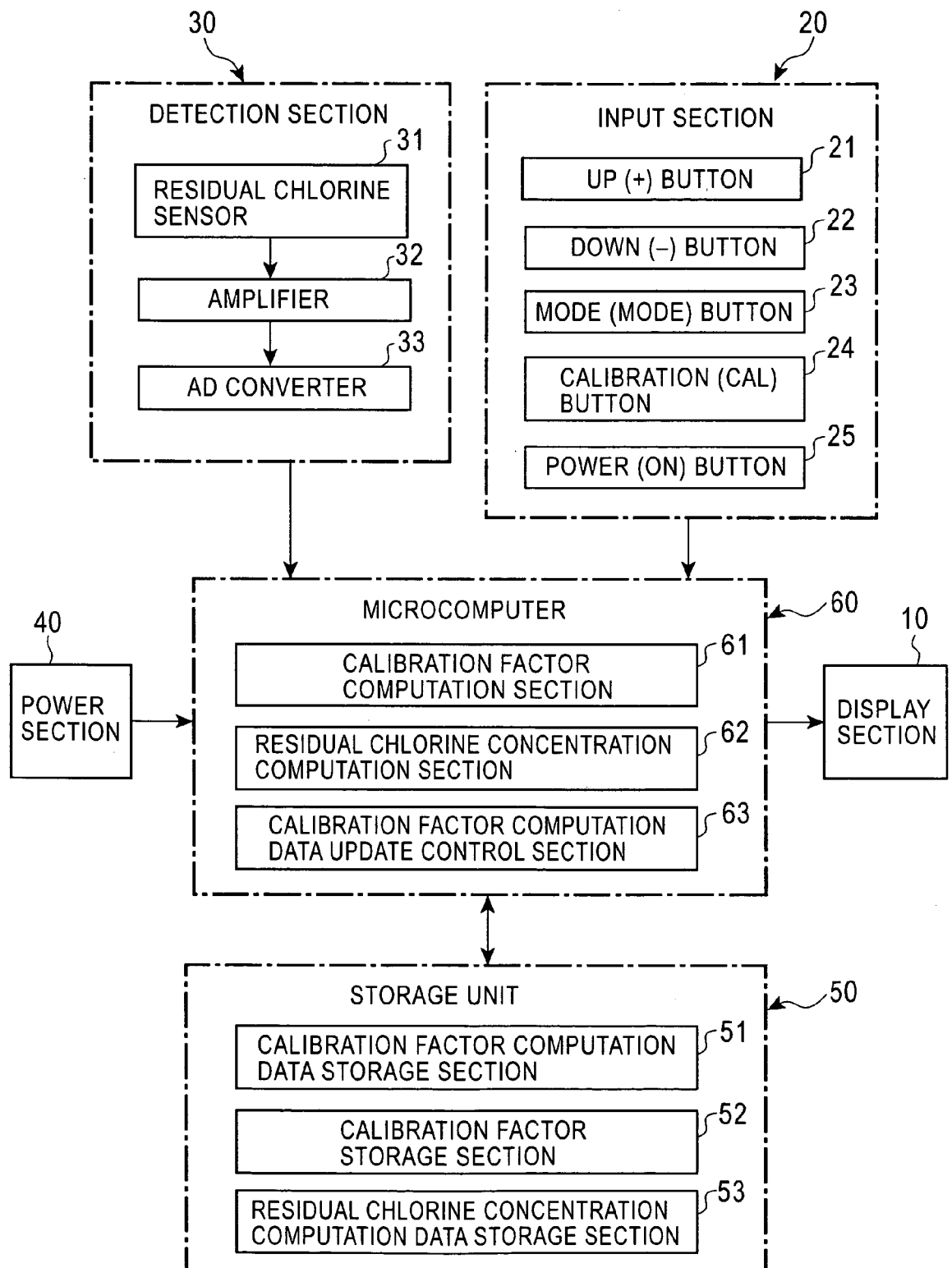
FIG. 2 is a block diagram showing the residual chlorine meter (Embodiments 1 and 2).

Firstly, the constitution of a residual chlorine meter (capable of calibrating the degree of influence by the pH of sample water) of Embodiment 1 will be described by use of a front view shown in FIG. 1 and a block diagram shown in FIG. 2.

The residual chlorine meter of Embodiment 1 apparently comprises a main unit 1 which has a display section 10 and an input section 20 on the front face of a box-shaped case 4, a sensor unit 2 which has a residual chlorine sensor 31 at the tip of a stick-shaped case 5, and a cable 3 which connects the sensor unit 2 to the main unit 1. The residual chlorine meter has an electronic substrate comprising an amplifier 32, an AD converter 33, a storage unit 50 and a microcomputer 60 and a power section 40 in the main unit 1. These components roughly constitute the whole residual chlorine meter.

The input section 20 comprises a power (ON) button 25, a calibration (CAL) button 24, a mode (MODE) button 23, an UP (+) button 21 and a DOWN (−) button 22 and makes inputs for starting, switching, setting and registration, and the like. In particular, the power (ON) button 25 and the calibration (CAL) button 24 make inputs for staring in a calibration mode. The power (ON) button 25 and the mode (MODE) button 23 make inputs for staring in a replacement mode. The UP (+) button 21, the DOWN (−) button 22 and the calibration (CAL) button 24 make inputs for setting and registering the calibration standard residual chlorine concentration (residual chlorine concentration of sample water measured by a DPD reagent type residual chlorine meter (different device from the residual chlorine meter of the present invention)) of sample water and the characteristic value of a sensor after replacement.

The display section 10 displays an input status, measurement results, various modes, remaining battery power, and the like.

The stick-shaped case 5 of the sensor unit 2 has, in addition to the residual chlorine sensor 31, a clip 6 for clipping a breast pocket when carrying the meter and a protective cap 7 for protecting the residual chlorine sensor 31 when it is not used.

The power section 40 supplies electric power to the components in the electrical system of the present device.

The amplifier 32 amplifies the pre-calibration residual chlorine reaction amount and on-measurement residual chlorine reaction amount (analog signals) of sample water which are detected by the residual chlorine sensor 31. The AD converter 33 converts the amplified pre-calibration residual chlorine reaction amount and on-measurement residual chlorine reaction amount of the sample water to digital signals. The residual chlorine sensor 31, the amplifier 32 and the AD converter 33 constitute a detection section 30. That is, the detection section 30 detects the pre-calibration residual chlorine reaction amount and on-measurement residual chlorine reaction amount of sample water.

The storage unit 50 comprises a calibration factor computation data storage section 51, a calibration factor storage section 52 and a residual chlorine concentration computation data storage section 53 and stores various data.

The calibration factor computation data storage section 51 stores data (the standard table shown in FIG. 11 and the following computing equations (1) and (2)) for computing calibration factors based on the pre-calibration residual chlorine reaction amount and calibration standard residual chlorine concentration of sample water in advance.

$$KDN = VSS/VSB \quad (1)$$

$$KUP = VSS/VSB \quad (2)$$

In the above computing equations, KDN represents a calibration factor when the concentration is lower than a selected standard residual chlorine concentration, KUP represents a calibration factor when the concentration is equal to or higher than the selected standard residual chlorine concentration, VSS represents a calibration standard residual chlorine reaction amount, and VSB represents a pre-calibration residual chlorine reaction amount.

The calibration factor storage section 52 stores calibration factors computed by a calibration factor computation section 61 to be described later.

The residual chlorine concentration computation data storage section 53 stores data (the standard table shown in FIG. 11 and the following computing equations (3), (4) and (5)) for computing the post-calibration residual chlorine concentration of sample water based on the on-measurement residual chlorine reaction amount of the sample water and the calibration factor in advance.

$$VSCA = VSCB \times VSM/VSS \quad (3)$$

$$VSAD = VSM/KDN \quad (4)$$

$$VSAU = VSM/KUP \quad (5)$$

In the above computing equations, VSCA represents a post-calibration selected standard residual chlorine reaction amount, VSCB represents a pre-calibration selected standard residual chlorine reaction amount, VSM represents an on-measurement residual chlorine reaction amount, VSS represents a calibration standard residual chlorine reaction amount, VSAD represents a post-calibration residual chlorine reaction amount when the concentration is lower than a selected standard residual chlorine concentration, KDN represents a calibration factor when the concentration is lower than the selected standard residual chlorine concentration, VSAU represents a post-calibration residual chlorine reaction amount when the concentration is equal to or higher than the selected standard residual chlorine concentration, and KUP represents a calibration factor when the concentration is equal to or higher than the selected standard residual chlorine concentration.

Figure 10:
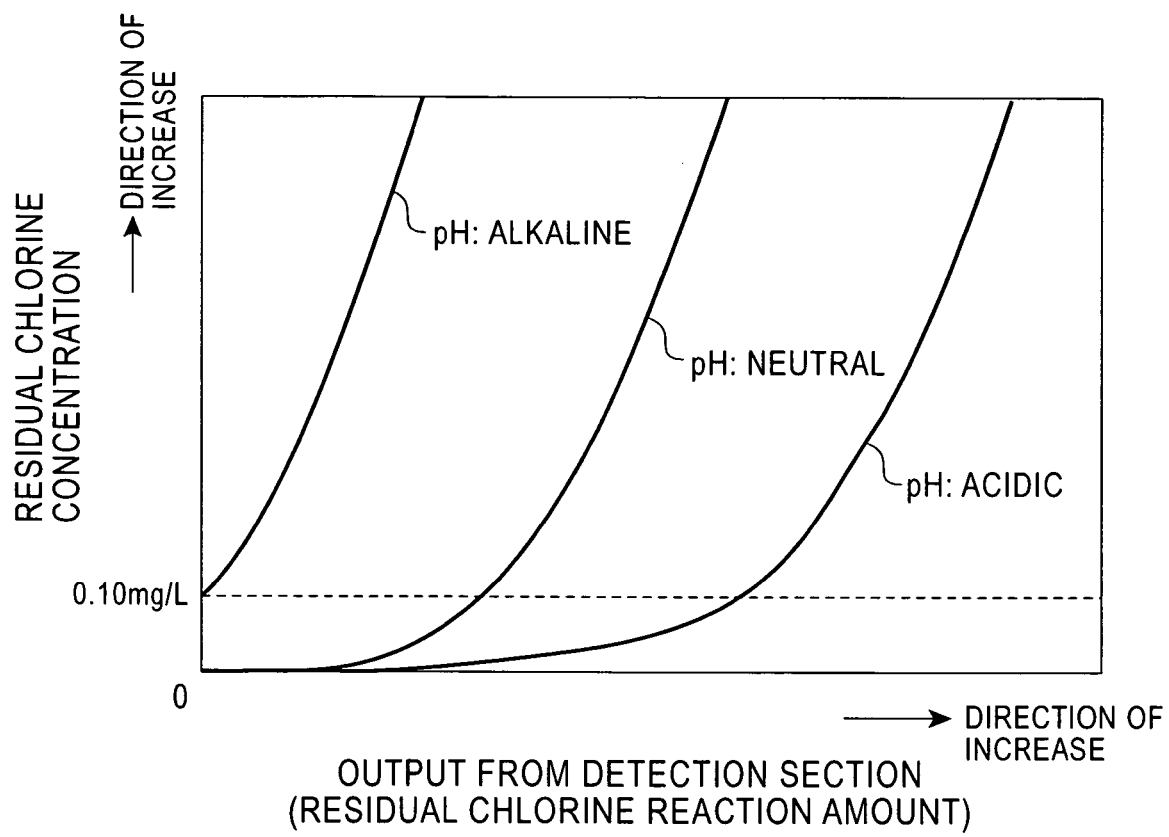
FIG. 10 is a graph showing the relationship among the residual chlorine concentration, the residual chlorine reaction amount and the pH (Embodiment 1).

The reason that the computing equations (1) and (2) and the computing equations (4) and (5) are formed as separate equations with the selected standard residual chlorine concentration as a boundary is as follows. As shown in the graph of FIG. 10, when the relationship between the residual chlorine concentration and the residual chlorine reaction amount is lower than the selected standard residual chlorine concentration (which is 0.10 mg/L in the present embodiment), the slope of the graph according to the pH of sample water changes remarkably, while when it is higher than the selected standard residual chlorine concentration (which is 0.10 mg/L in the present embodiment), the slope of the graph according to the pH of the sample water remains almost unchanged.

The microcomputer 60 comprises a calibration factor computation section 61, a residual chlorine concentration computation section 62 and a calibration factor computation data update control section 63 and computes and controls various data.

The calibration factor computation section 61 computes calibration factors based on the pre-calibration residual chlorine reaction amount of sample water detected by the detection section 30, the calibration standard residual chlorine concentration of the sample water input through the input section 20, and the data for computing the calibration factors which are stored in advance in the calibration factor computation data storage section 51.

More specifically, the section 61 refers to the standard table shown in FIG. 11, specifies, as a calibration standard residual chlorine reaction amount (VSS), a residual chlorine reaction amount which corresponds to a residual chlorine concentration corresponding to the calibration standard residual chlorine concentration of the sample water input through the input section 20, and substitutes the specified calibration standard residual chlorine reaction amount (VSS) and the pre-calibration residual chlorine reaction amount (VSB) of the sample water detected by the detection section 30 into the computing equations (1) and (2) stored in advance in the calibration factor computation data storage section 51 so as to compute the calibration factors (KDN and KUP).

The residual chlorine concentration computation section 62 computes the post-calibration residual chlorine concentration of the sample water based on the on-measurement residual chlorine reaction amount of the sample water detected by the detection section 30, the calibration factor stored in the calibration factor storage section 52, and the data for computing the post-calibration residual chlorine concentration of the sample water stored in advance in the residual chlorine concentration computation data storage section 53.

More specifically, firstly, the section 62 refers to the standard table shown in FIG. 11 so as to specify a pre-calibration selected standard residual chlorine reaction amount (VSCB) for selecting the computing equation (4) or (5), and substitutes the specified pre-calibration selected standard residual chlorine reaction amount (VSCB), the calibration standard residual chlorine reaction amount (VSS) specified in advance in the calibration factor computation section 61 and the on-measurement residual chlorine reaction amount (VSM) of the sample water detected in advance by the detection section 30 into the computing equation (3) stored in advance in the residual chlorine concentration computation data storage section 53 so as to compute a post-calibration selected standard residual chlorine reaction amount (VSCA).

Then, when the computed post-calibration selected standard residual chlorine reaction amount (VSCA) is equal to or higher than the on-measurement residual chlorine reaction amount (VSM) of the sample water detected by the detection section 30 by the measurement after computations of the calibration factors (VSCA≧VSM), the section 62 selects the computing equation (4), while when VSCA is lower than VSM (VSCA<VSM), the section 62 selects the computing equation (5).

Then, the section 62 substitutes the calibration factor (KDN or KUP) computed in advance by the calibration factor computation section 61 and the on-measurement residual chlorine reaction amount (VSM) of the sample water detected by the detection section 30 by the measurement after computations of the calibration factors into the above selected computing equation (4) or (5) so as to compute a post-calibration residual chlorine reaction amount (VSAD or VSAU).

Then, the section 62 refers to the standard table shown in FIG. 11 and specifies, as a post-calibration residual chlorine concentration, a residual chlorine concentration which corresponds to a residual chlorine reaction amount corresponding to the post-calibration residual chlorine reaction amount (VSAD or VSAU).

The calibration factor computation data update control section 63 updates the data for computing the calibration factors stored in the calibration factor computation data storage section 51, when a characteristic value representing the characteristic of the residual chlorine sensor 31 is input from the input section 20.

More specifically, in the calibration factor computation section 61, residual chlorine reaction amounts in the standard table shown in FIG. 11 are multiplied by a coefficient corresponding to the characteristic value of a replaced sensor 31 so as to update the standard table shown in FIG. 11 which is stored in the calibration factor computation data storage section 51.

Figure 3:
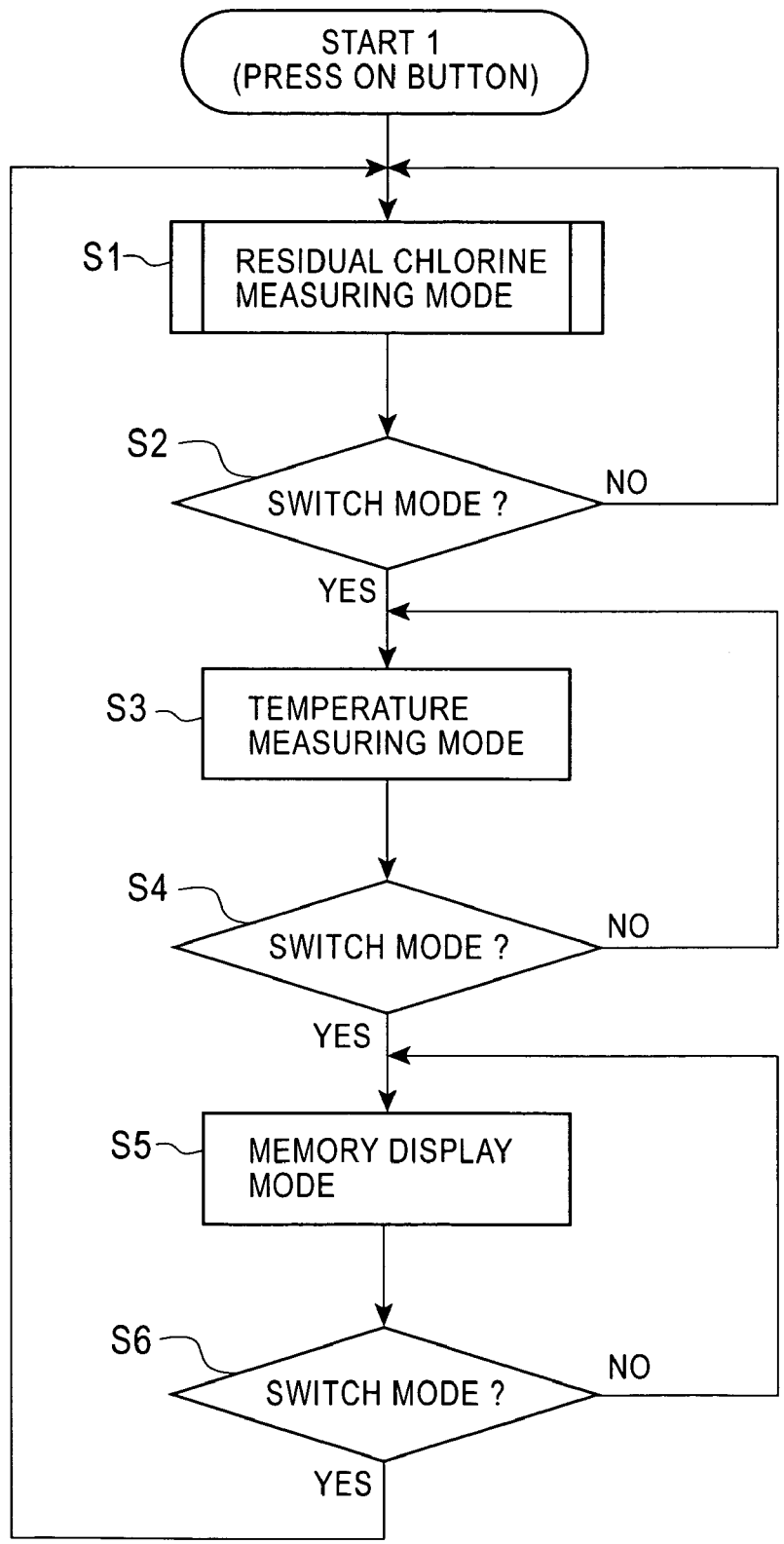
FIG. 3 is a main flowchart in the normal mode of the residual chlorine meter (Embodiments 1 and 2).
Figure 4A:
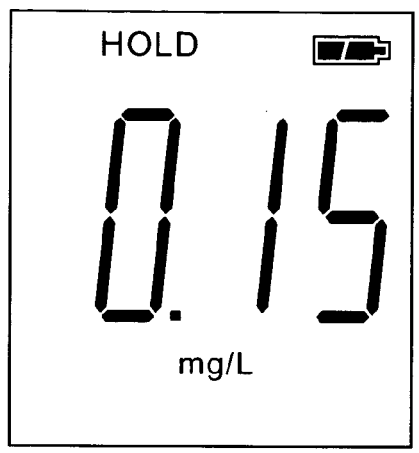
FIG. 4 is a diagram showing a display example in the normal mode (Embodiments 1 and 2).
Figure 4B:
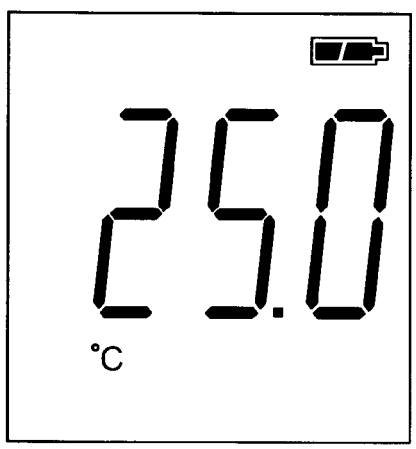
Figure 4C:
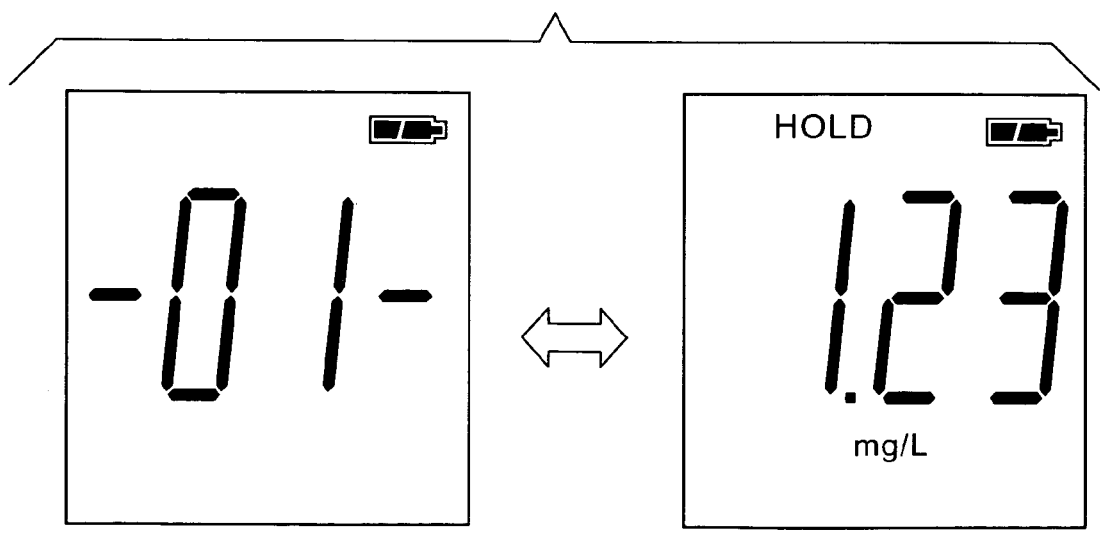
Figure 5:
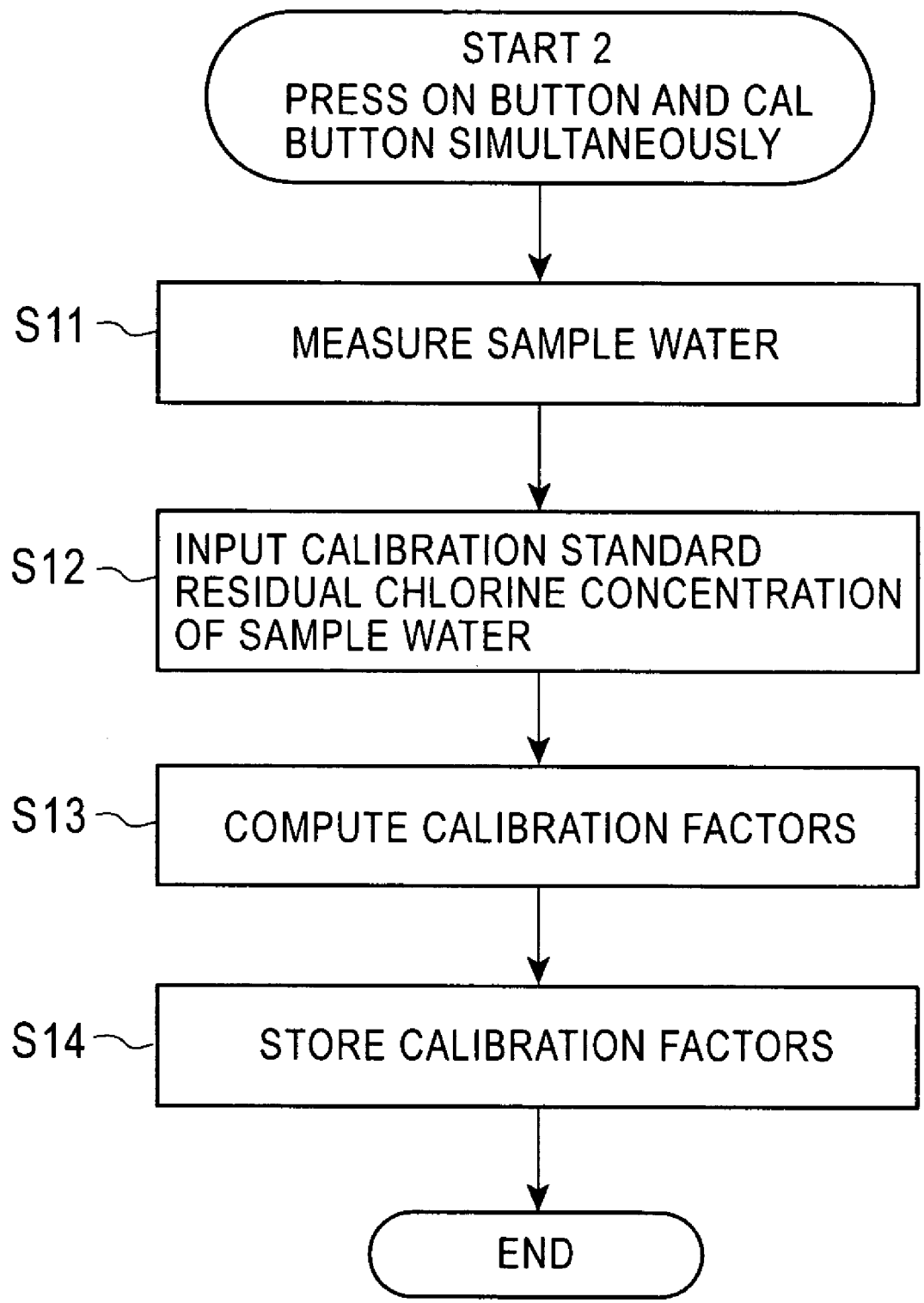
FIG. 5 is a flowchart in the calibration mode of the residual chlorine meter (Embodiment 1).
Figure 6A:
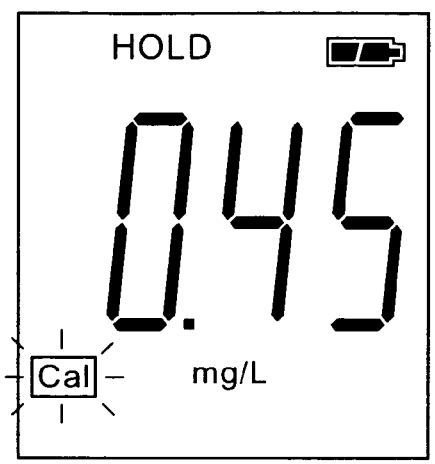
FIG. 6 is a diagram showing a display example in the calibration mode (Embodiment 1).
Figure 6B:
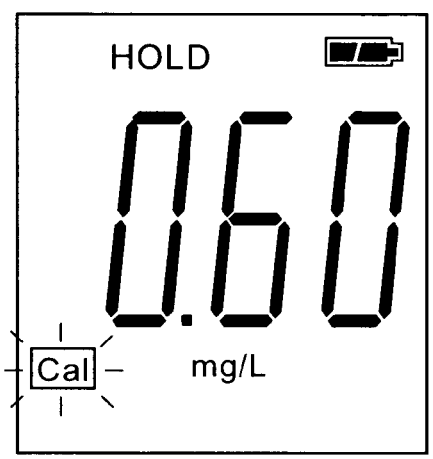
Figure 6C:
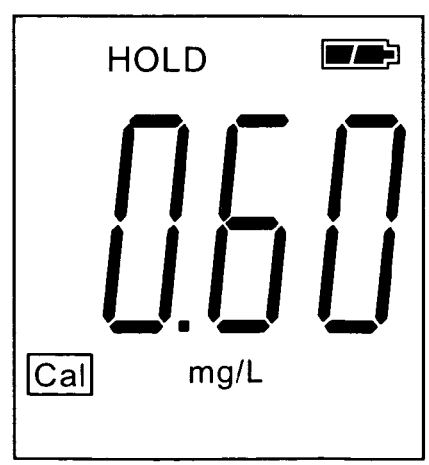

Next, the operations of the residual chlorine meter of the present invention will be described by use of flowcharts shown in FIGS. 3, 5, 7 and 9 and display examples shown in FIGS. 4, 6 and 8.

Firstly, operations in a normal mode will be described in detail with reference to FIGS. 3 and 4. At the press of the power (ON) button 25, electric power is supplied from the power section 40 to each component in the electrical system, and the present device is activated in a residual chlorine concentration measuring mode, thereby making possible measurement of a residual chlorine concentration. A user removes the protective cap 7 of the sensor unit 2, immerses the residual chlorine sensor 31 in sample water, and measures the residual chlorine concentration while stirring the water. Upon passage of a predetermined amount of time (about 15 seconds) after immersion, the result of the measurement is displayed as shown in FIG. 4(*a*) (the residual chlorine concentration is held with "HOLD" blinking) (STEP S1). Detailed operations in this residual chlorine concentration measuring mode will be described later.

Then, in this residual chlorine concentration measuring mode, if the mode (MODE) button 23 is not pressed (NO in STEP S2), this residual chlorine concentration measuring mode is continued. Meanwhile, if the mode (MODE) button 23 is pressed (YES in STEP S2), the present device enters a temperature measuring mode, measures the temperature by use of the residual chlorine sensor 31 (which also serves as a temperature sensor) and displays the measurement result (temperature) as shown in FIG. 4(*b*) (STEP S3).

Then, in this temperature measuring mode, if the mode (MODE) button 23 is not pressed (NO in STEP S4), this temperature measuring mode is continued. Meanwhile, if the mode (MODE) button 23 is pressed (YES in STEP S4), the present device enters a memory display mode and blinks a stored data registration number (-01-) and a residual chlorine concentration (1.23) which have been measured and stored in the past alternately as shown in FIG. 4(*c*) (STEP S5). At this point, at the press of the UP (+) button 21 or the DOWN (−) button 22, the stored data registration number is switched to a subsequent stored data registration number, and the subsequent stored data registration number and a residual chlorine concentration corresponding thereto are blinked alternately.

Then, in this memory display mode, if the mode (MODE) button 23 is not pressed (NO in STEP S6), this memory display mode is continued. Meanwhile, if the mode (MODE) button 23 is pressed (YES in STEP S6), the present device is switched to the residual chlorine concentration measuring mode (STEP S1) and repeats the foregoing processes.

Secondly, operations in a calibration mode will be described in detail with reference to FIGS. 5 and 6. At the concurrent presses of the power (ON) button 25 and the calibration (CAL) button 24, electric power is supplied from the power section 40 to each component in the electrical system, and the present device is activated in a calibration mode, whereby "CAL" in the display section 10 blinks and calibration can be so conducted as to obtain a result (residual chlorine concentration) corresponding to the pH of sample water. A user removes the protective cap 7 of the sensor unit 2, immerses the residual chlorine sensor 31 in sample water and makes a measurement while stirring the water. Upon passage of a predetermined amount of time (about 15 seconds) after immersion, the result of the measurement before calibration is displayed as shown in FIG. 6(a) (the pre-calibration residual chlorine concentration is held with "HOLD" blinking) (STEP S11).

Then, the user measures the sample water by use of a DPD reagent type residual chlorine meter (different device from the residual chlorine meter of the present invention). Then, when the thus obtained residual chlorine concentration (calibration standard residual chlorine concentration) is input from the UP (+) button 21 or the DOWN (−) button 22 of the present residual chlorine meter, the calibration standard residual chlorine concentration is displayed as shown in FIG. 6(b) (STEP S12).

Then, when the calibration (CAL) button 24 is pressed, the calibration factor computation section 61 refers to the standard table shown in FIG. 11 and specifies, as a calibration standard residual chlorine reaction amount (VSS), a residual chlorine reaction amount which corresponds to a residual chlorine concentration corresponding to the calibration standard residual chlorine concentration input from the UP (+) button 21 or the DOWN (−) button 22. Then, the section 61 substitutes the specified calibration standard residual chlorine reaction amount (VSS) and the pre-calibration residual chlorine reaction amount (VSB) of the sample water detected by the detection section 30 in STEP S11 into the computing equations (1) and (2) stored in advance in the calibration factor computation data storage section 51 so as to compute calibration factors (KDN and KUP) (STEP S13).

Then, the calibration factor storage section 52 stores the calibration factors (KDN and KUP) computed by the calibration factor computation section 61 (STEP S14).

Figure 8A:
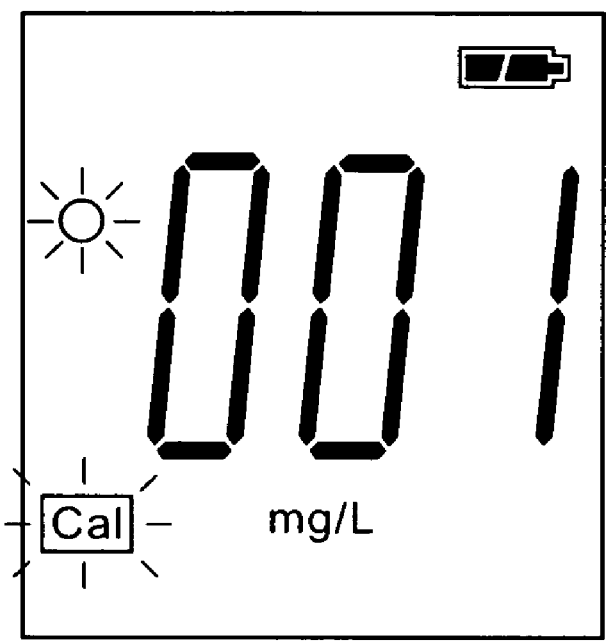
FIG. 8 is a diagram showing a display example in the replacement mode (Embodiments 1 and 2).
Figure 8B:
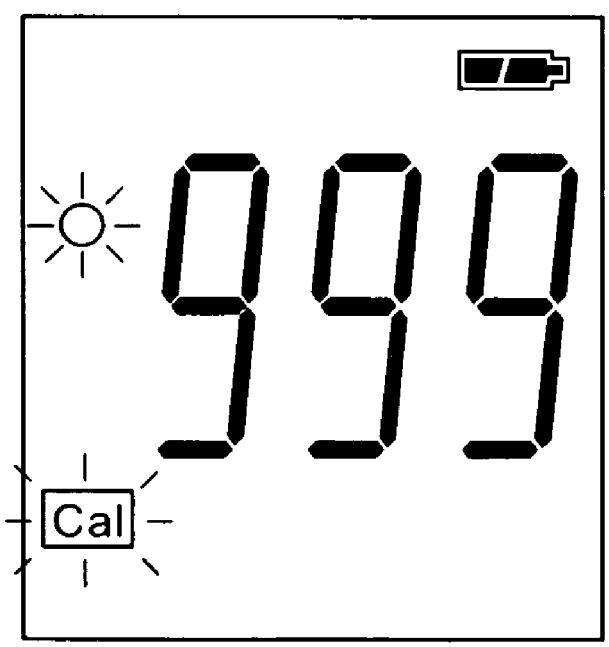

Thirdly, operations in a replacement mode will be described in detail with reference to FIGS. 7 and 8. At the concurrent presses of the power (ON) button 25 and the mode (MODE) button 23, electric power is supplied from the power section 40 to each component in the electrical system, and the present device is activated in a replacement mode, whereby "CAL" and "○" in the display section 10 blink simultaneously as shown in FIG. 8(a) and the characteristic value of a newly replaced residual chlorine sensor 31 can be set and registered. Then, when the characteristic value of the replaced residual chlorine sensor 31 is input from the UP (+) button 21 or the DOWN (−) button 22, the characteristic value of the replaced residual chlorine sensor 31 is displayed as shown in FIG. 8(b) (STEP S21).

Then, when the calibration (CAL) button 24 is pressed, the calibration factor computation data update control section 63 updates data for computing calibration factors based on the residual chlorine reaction amount and residual chlorine standard concentration of sample water, by the characteristic value of the replaced residual chlorine sensor 31. More specifically, in the calibration factor computation section 61, residual chlorine reaction amounts in the standard table shown in FIG. 11 are multiplied by a coefficient corresponding to the characteristic value of the replaced residual chlorine sensor 31 so as to update the standard table shown in FIG. 11 which is stored in the calibration factor computation data storage section 51 (STEP S22).

Figure 9:
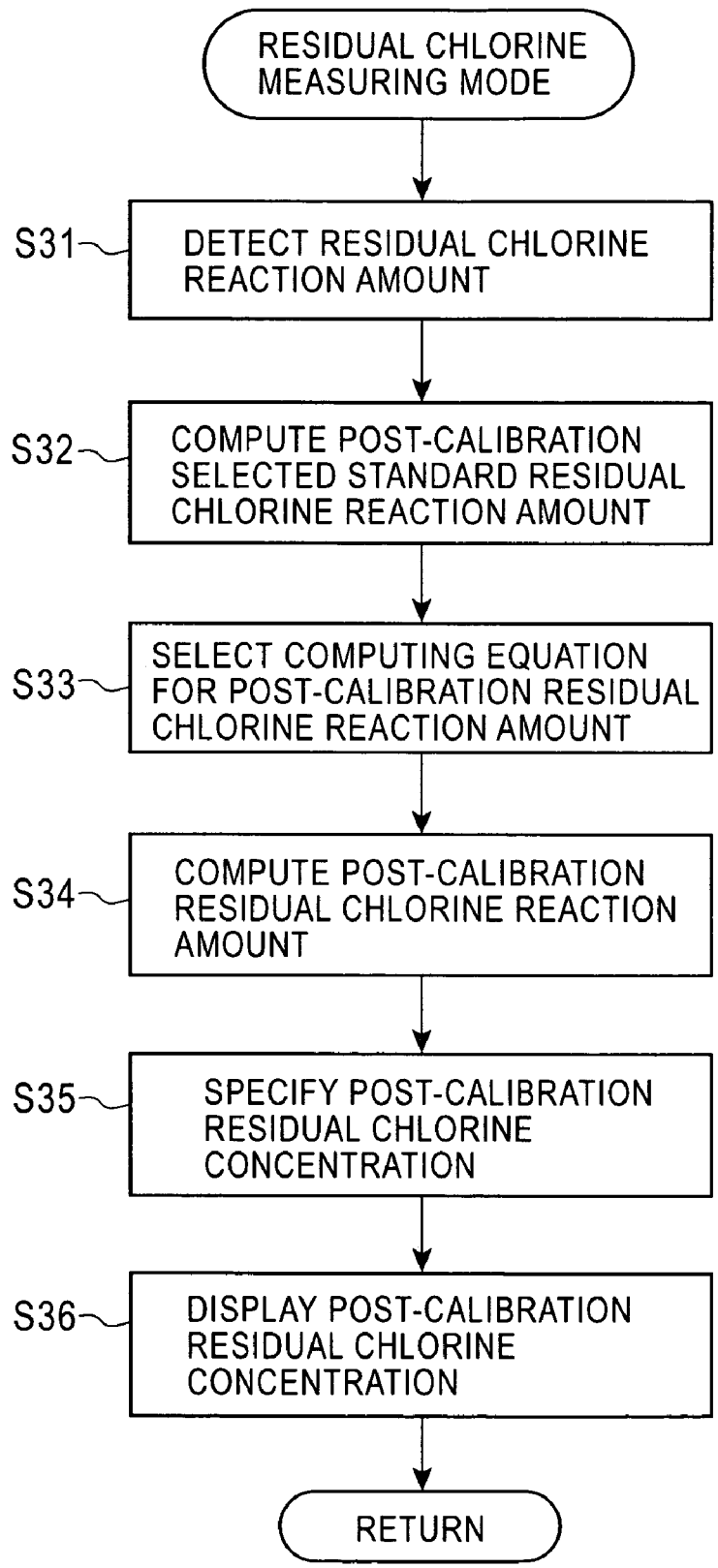
FIG. 9 is a subroutine flowchart in the normal mode of the residual chlorine meter (Embodiment 1).

Fourthly, operations in the residual chlorine concentration measuring mode described with respect to the above normal mode will be described in detail with reference to FIG. 9. When the power (ON) button 25 is pressed, the present device is activated in the residual chlorine concentration measuring mode and the residual chlorine sensor 31 is immersed in sample water, the residual chlorine reaction amount of the sample water is output from the detection section 30 (STEP S31)

Then, the residual chlorine concentration computation section 62 firstly refers to the standard table shown in FIG. 11 to specify a pre-calibration selected standard residual chlorine reaction amount (VSCB) for selecting the computing equation (4) or (5), and substitutes the specified pre-calibration selected standard residual chlorine reaction amount (VSCB), the calibration standard residual chlorine reaction amount (VSS) specified in advance in the calibration factor computation section 61 and the on-measurement residual chlorine reaction amount (VSM) of the sample water detected in advance by the detection section 30 into the computing equation (3) stored in advance in the residual chlorine concentration computation data storage section 53 so as to compute a post-calibration selected standard residual chlorine reaction amount (VSCA) (STEP S32).

Then, when the computed post-calibration selected standard residual chlorine reaction amount (VSCA) is equal to or higher than the on-measurement residual chlorine reaction amount (VSM) of the sample water detected by the detection section 30 by the measurement after computations of the calibration factors (VSCA≧VSM), the section 62 selects the computing equation (4), while when VSCA is lower than VSM (VSCA<VSM), the section 62 selects the computing equation (5) (STEP S33).

Then, the section 62 substitutes the calibration factor (KDN or KUP) computed in advance by the calibration factor computation section 61 and the on-measurement residual chlorine reaction amount (VSM) of the sample water detected by the detection section 30 by the measurement after computations of the calibration factors into the above selected computing equation (4) or (5) so as to compute a post-calibration residual chlorine reaction amount (VSAD or VSAU) (STEP S34).

Then, the section 62 refers to the standard table shown in FIG. 11 and specifies, as a post-calibration residual chlorine concentration, a residual chlorine concentration which corresponds to a residual chlorine reaction amount corresponding to the post-calibration residual chlorine reaction amount (VSAD or VSAU) (STEP S35).

Then, the section 62 displays the specified post-calibration residual chlorine concentration (STEP S36).

As described above, as a preparatory stage for measurements, the residual chlorine meter in the first embodiment detects the pre-calibration residual chlorine reaction amount of sample water in the detection section 30, inputs a calibration standard residual chlorine concentration in the input section 20, determines calibration factors from data for computing the calibration factors based on the pre-calibration residual chlorine reaction amount and calibration standard residual chlorine standard concentration of the sample water stored in the calibration factor computation data storage section 51 in the calibration factor computation section 61, and stores the calibration factors in the calibration factor storage section 52. Then, as a measurement stage, the residual chlorine meter detects the on-measurement residual chlorine reaction amount of the sample water in the detection section 30 and determines the post-calibration residual chlorine concentration of the sample water from data for computing the post-calibration residual chlorine concentration of the sample water based on the on-measurement residual chlorine reaction amount of the sample water and the calibration factor stored in the residual chlorine concentration computation data storage section 53 in the residual chlorine concentration computation section 62, thereby calibrating the degree of influence by the pH of the sample water.

[Embodiment]2

Firstly, the constitution of a residual chlorine meter (capable of calibrating the degree of influence by the electric conductivity of sample water) of the present invention will be described by use of a front view shown in FIG. 1 and a block diagram shown in FIG. 2. As shown in FIGS. 1 and 2, the constituents of the residual chlorine meter of Embodiment 2 are the same as those of the residual chlorine meter of Embodiment 1. Thus, only different constituents therebetween will be described in detail.

The calibration factor computation data storage section 51 stores in advance data (the following computing equations (6) and (7)) for computing calibration factors based on the pre-calibration residual chlorine reaction amount and calibration standard residual chlorine standard concentration of sample water.

$$KDN = \sqrt{VDS/A} - VSB \quad (6)$$

$$KUP = \sqrt{VDS/C} - VSB - VSCB \quad (7)$$

In the above computing equations, KDN represents a calibration factor when the concentration is lower than a selected standard residual chlorine concentration, KUP represents a calibration factor when the concentration is equal to or higher than the selected standard residual chlorine concentration, VDS represents a calibration standard residual chlorine concentration (which is 0 mg/L in the present embodiment because the present embodiment uses sample water without a residual chlorine concentration as a standard), A and C represent coefficients (specified values), VSB represents a pre-calibration residual chlorine reaction amount, and VSCB represents a pre-calibration selected standard residual chlorine reaction amount (specified value).

The residual chlorine concentration computation data storage section 53 stores in advance data (the following computing equations (8) and (9), and a selected standard residual chlorine reaction amount (VSC) corresponding to a selected standard residual chlorine concentration) for computing the post-calibration residual chlorine concentration of the sample water based on the on-measurement residual chlorine reaction amount of the sample water and the calibration factor.

$$VDAD = A(VSM - KDN)^2 \quad (8)$$

$$VDAU = C(VSM - KUP)^2 + VDSS \quad (9)$$

In the above computing equations, VDAD represents a post-calibration residual chlorine concentration when the concentration is lower than a selected standard residual chlorine concentration, VDAU represents a post-calibration residual chlorine concentration when the concentration is equal to or higher than the selected standard residual chlorine concentration, A and C represent coefficients (specified values), VSM represents an on-measurement residual chlorine reaction amount, KDN represents a calibration factor when the concentration is lower than the selected standard residual chlorine concentration, KUP represents a calibration factor when the concentration is equal to or higher than the selected standard residual chlorine concentration, and VDSS represents the selected standard residual chlorine concentration (which is 0.20 mg/L in the present embodiment).

Figure 12:
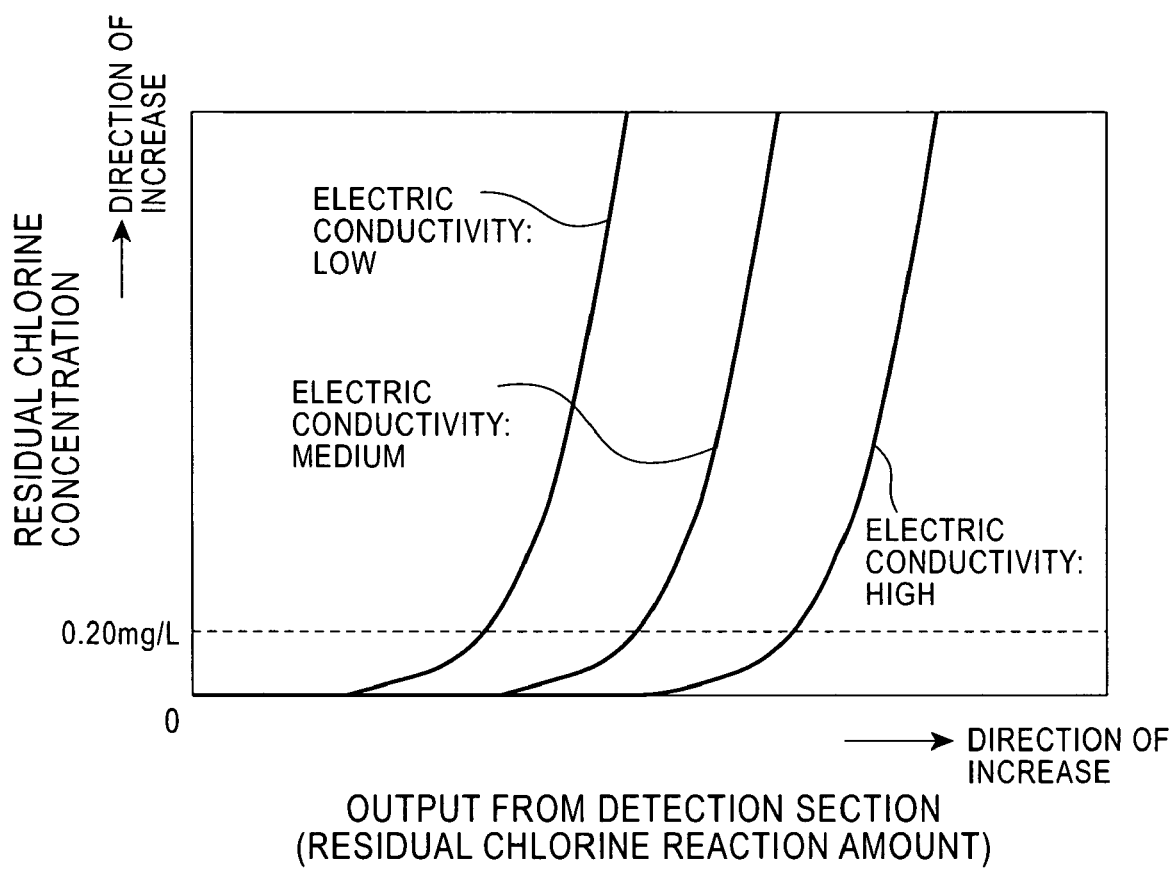
FIG. 12 is a graph showing the relationship among the residual chlorine concentration, the residual chlorine reaction amount and the electric conductivity (Embodiment 1)

The reason that the computing equations (6) and (7) and the computing equations (8) and (9) are formed as separate equations with the selected standard residual chlorine concentration as a boundary is as follows. That is, as shown in the graph of FIG. 12, the slope of the graph representing the relationship between the residual chlorine concentration and the residual chlorine reaction amount changes at the selected standard residual chlorine concentration (which is 0.20 mg/L in the present embodiment).

The calibration factor computation section 61 computes calibration factors based on the pre-calibration residual chlorine reaction amount of sample water detected by the detection section 30 and the data stored in advance in the calibration factor computation data storage section 51.

More specifically, the calibration mode is activated by the input section 20, and the section 61 substitutes the pre-calibration residual chlorine reaction amount (VSB) of the sample water detected by the detection section 30 into the computing equations (6) and (7) stored in advance in the calibration factor computation data storage section 51 so as to compute the calibration factors (KDN and KUP).

The residual chlorine concentration computation section 62 computes the post-calibration residual chlorine concentration of the sample water based on the on-measurement residual chlorine reaction amount of the sample water detected by the detection section 30, the calibration factor stored in the calibration factor storage section, and the data stored in advance in the residual chlorine concentration computation data storage section 53.

More specifically, firstly, when the selected standard residual chlorine reaction amount (VSC) stored in advance in the residual chlorine concentration computation data storage section 53 is equal to or higher than the on-measurement residual chlorine reaction amount (VSM) of the sample water detected by the detection section 30 (VSC≧VSM), the section 62 selects the computing equation (8), while when VSC is lower than VSM (VSC<VSM), the section 62 selects the computing equation (9).

Then, the section 62 substitutes the calibration factor (KDN or KUP) computed in advance by the calibration factor computation section 61 and the on-measurement residual chlorine reaction amount (VSM) of the sample water detected by the detection section 30 by the measurement after computations of the calibration factors into the above selected computing equation (8) or (9) to compute a post-calibration residual chlorine concentration (VDAD or VDAU).

Figure 13:
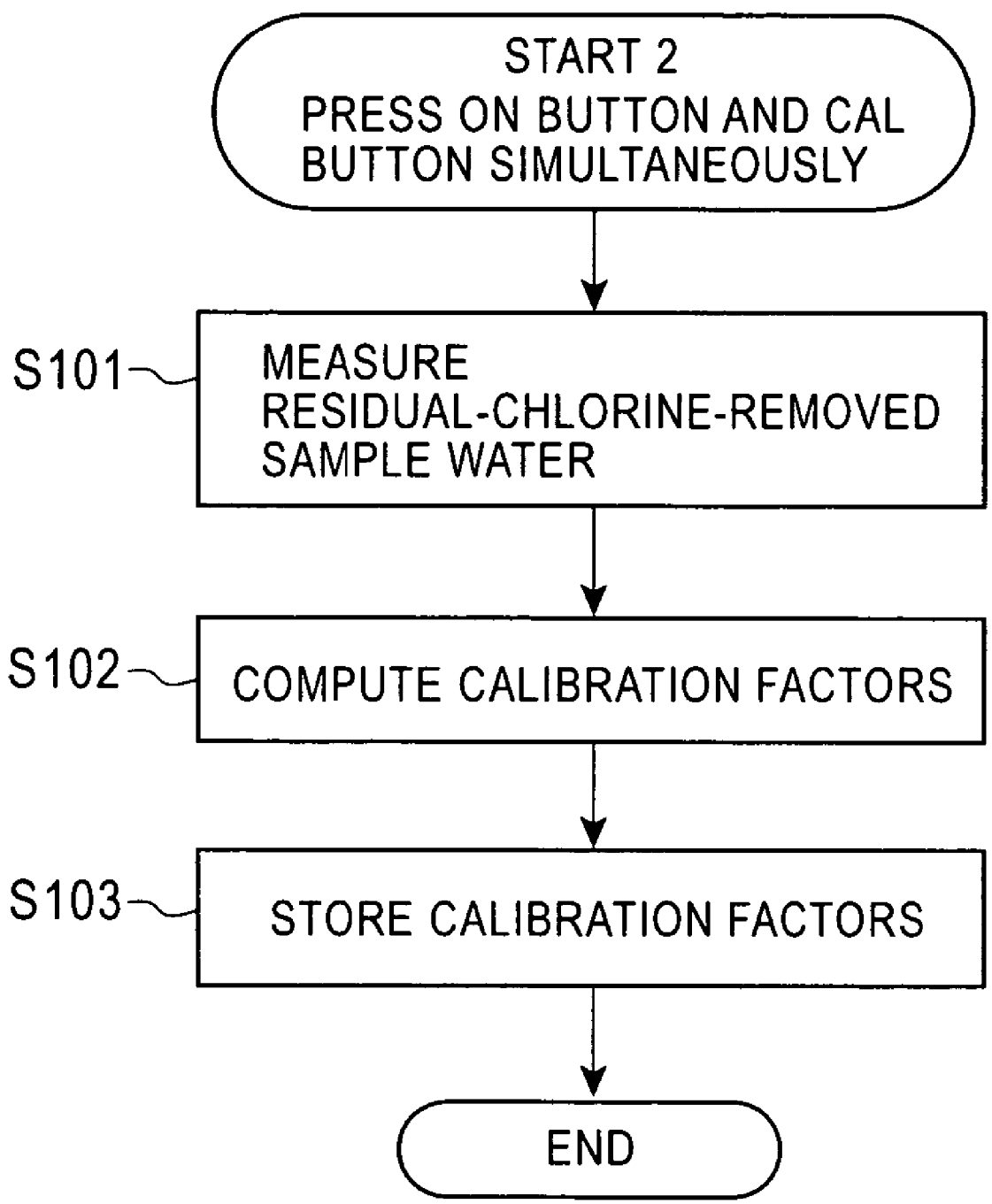
FIG. 13 is a flowchart in the calibration mode of the residual chlorine meter (Embodiment 2).
Figure 14:
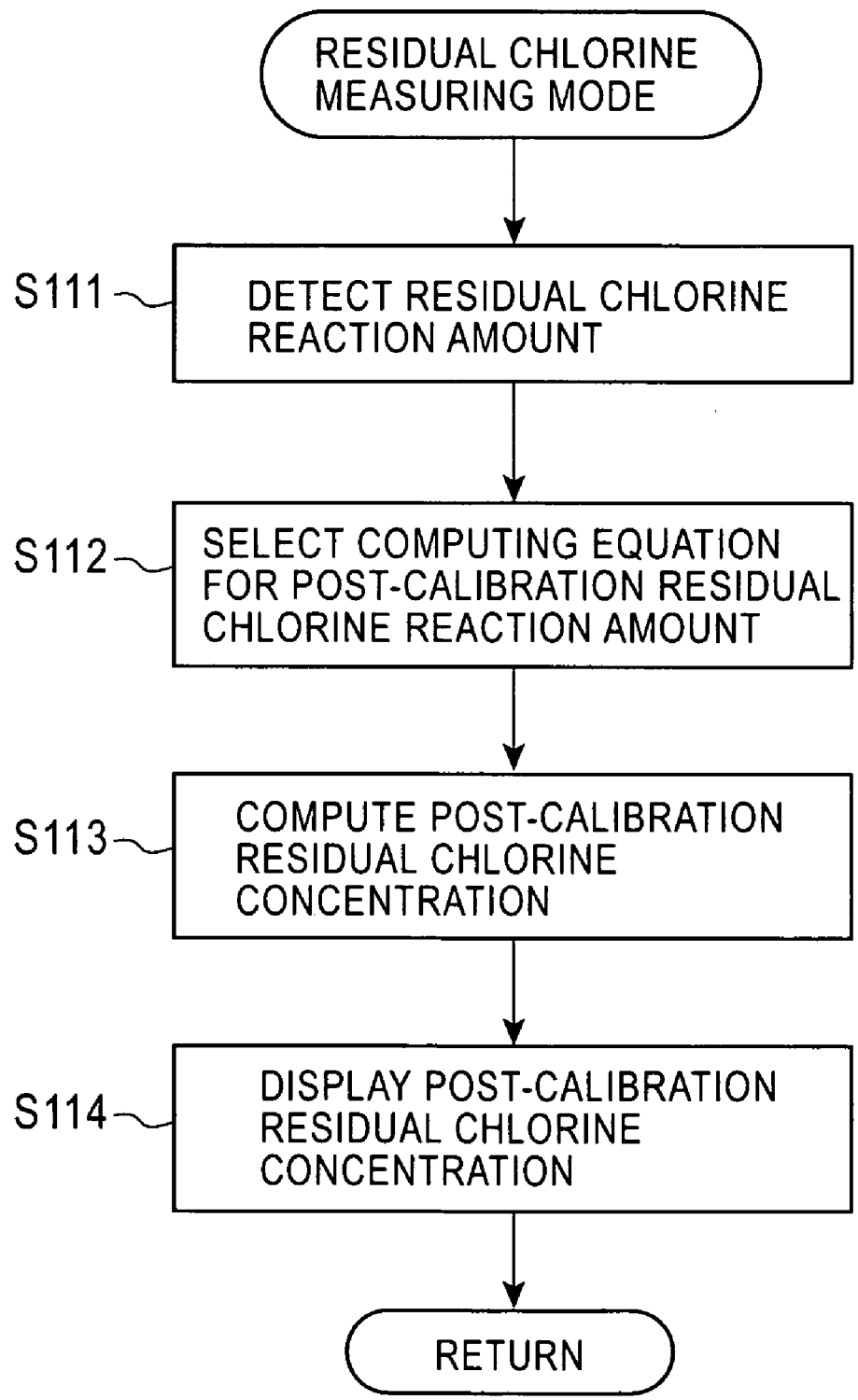
FIG. 14 is a subroutine flowchart in the normal mode of the residual chlorine meter (Embodiment 2).

Next, the operations of the residual chlorine meter of Embodiment 2 will be described by use of flowcharts shown in FIGS. 13 and 14. The residual chlorine meter of Embodiment 2 also undergoes the same processes in the flowcharts shown in FIGS. 3 and 7 as those which the residual chlorine meter of Embodiment 1 undergoes. Hence, detailed descriptions of the processes will be omitted.

Firstly, operations in a calibration mode will be described in detail with reference to FIG. 13. At the concurrent presses of the power (ON) button 25 and the calibration (CAL) button 24, electric power is supplied from the power section 40 to each component in the electrical system, and the present device is activated in a calibration mode, whereby "CAL" in the display section 10 blinks and calibration can be so conducted as to obtain a result (residual chlorine concentration) corresponding to the electric conductivity of sample water. A user removes the protective cap 7 of the sensor unit 2, immerses the residual chlorine sensor 31 in sample water which has been boiled, left to stand, purified or subjected to other treatment so as to remove residual chlorine therefrom (i.e., adjust the residual chlorine concentration to 0 mg/L) and makes a measurement while stirring the water (STEP S101).

Then, after passage of a predetermined amount of time (about 15 seconds) after immersion, the calibration factor computation section 61 substitutes the pre-calibration residual chlorine reaction amount (VSB) of the sample water detected by the detection section 30 into the computing equations (6) and (7) stored in advance in the calibration factor computation data storage unit 51 so as to compute calibration factors (KDN and KUP) (STEP S102).

Then, the calibration factor storage section 52 stores the calibration factors (KDN and KUP) computed by the calibration factor computation section 61 (STEP S103).

Fourthly, operations in the residual chlorine concentration measuring mode described with respect to the above normal mode will be described in detail with reference to FIG. 14. When the power (ON) button 25 is pressed, the present device is activated in the residual chlorine concentration measuring mode and the residual chlorine sensor 31 is immersed in sample water, the on-measurement residual chlorine reaction amount of the sample water is output from the detection section 30 (STEP S111).

Then, the residual chlorine concentration computation section 62 compares the on-measurement residual chlorine reaction amount (VSM) of the sample water detected by the detection section 30 with the selected standard residual chlorine reaction amount (VSC) stored in advance in the residual chlorine concentration computation data storage section 53. When VSC is equal to or higher than VSM (VSC≧VSM), the section 62 selects the computing equation (8), while when VSC is lower than VSM (VSC<VSM), the section 62 selects the computing equation (9) (STEP S112).

Then, the section 62 substitutes the calibration factor (KDN or KUP) computed in advance by the calibration factor computation section 61 and the on-measurement residual chlorine reaction amount (VSM) of the sample water detected by the detection section 30 by the measurement after computations of the calibration factors into the above selected computing equation (8) or (9) so as to compute a post-calibration residual chlorine concentration (VDAD or VDAU) (STEP S113).

Then, the section 62 displays the specified post-calibration residual chlorine concentration (STEP S114).

As described above, as a preparatory stage for measurements, the residual chlorine meter in the second embodiment detects the pre-calibration residual chlorine reaction amount of sample water in the detection section 30, determines calibration factors from data for computing the calibration factors based on the pre-calibration residual chlorine reaction amount and residual chlorine standard concentration of the sample water stored in the calibration factor computation data storage section 51 in the calibration factor computation section 61, and stores the calibration factors in the calibration factor storage section 52. Then, as a measurement stage, the residual chlorine meter detects the on-measurement residual chlorine reaction amount of the sample water in the detection section 30 and determines the post-calibration residual chlorine concentration of the sample water from data for computing the post-calibration residual chlorine concentration of the sample water based on the on-measurement residual chlorine reaction amount of the sample water and the calibration factor stored in the residual chlorine concentration computation data storage section 53 in the residual chlorine concentration computation section 62, thereby calibrating the degree of influence by the electric conductivity of the sample water.

The residual chlorine meter of the present invention may be so constituted as to perform the operations of Embodiments 1 and 2. In that case, the present residual chlorine meter is capable of calibrating the degree of influence by the pH and electric conductivity of sample water.

What is claimed is:

1. A residual chlorine meter comprising:
a detection section;
an input section;
a calibration factor computation data storage section;
a calibration factor computation section;
a calibration factor storage section;
a residual chlorine concentration computation data storage section; and
a residual chlorine concentration computation section;
wherein the detection section is for detecting a pre-calibration residual chlorine reaction amount and an on-measurement residual chlorine reaction amount of sample water;
wherein the input section is for selecting a calibration standard residual chlorine concentration of the sample water;
wherein the calibration factor computation data storage section is for storing, in advance, a standard table showing a relationship between a residual chlorine concentration and a residual chlorine reaction amount and including a selected standard residual chlorine concentration that indicates a borderline at which the trend in the relationship changes prominently; a computing equation for computing a calibration factor when the concentration is lower than the selected standard residual chlorine concentration, based on the pre-calibration residual chlorine reaction amount and the calibration standard residual chlorine concentration; and a computing equation for computing a calibration factor, when the concentration is equal to or higher than the selected standard residual chlorine concentration, based on the pre-calibration residual chlorine reaction amount and the calibration standard residual chlorine concentration;
wherein the calibration factor computation section refers to the standard table stored in the calibration factor computation data storage section to specify, as a calibration standard residual chlorine reaction amount, a residual chlorine reaction amount corresponding to a residual chlorine concentration corresponding to the calibration standard residual chlorine concentration of the sample water selected via the input section, and substitutes the specified calibration standard residual chlorine reaction amount and the pre-calibration residual chlorine reaction amount of the sample water into the computing equation for computing a calibration factor for when the concentration is lower than the selected standard residual chlorine concentration and into the computing equation for computing a calibration factor for when the concentration is equal to or higher than the selected standard residual chlorine concentration, to compute the calibration factor when the concentration is lower than the selected standard residual chlorine concentration and the calibration factor when the concentration is equal to or higher than the selected standard residual chlorine concentration;

wherein the calibration factor storage section stores the calibration factor for when the concentration is lower than the selected standard residual chlorine concentration and the calibration factor for when the concentration is equal to or higher than the selected standard residual chlorine concentration that have been computed by the calibration factor computation section;

wherein the residual chlorine concentration computation data storage section is for storing, in advance, a standard table showing a relationship between a residual chlorine concentration and a residual chlorine reaction amount and including a pre-calibration selected standard residual chlorine reaction amount corresponding to a selected standard residual chlorine concentration that indicates a borderline at which the trend in the relationship changes prominently; a computing equation for computing a post-calibration selected standard residual chlorine reaction amount based on the pre-calibration selected standard residual chlorine reaction amount, the on-measurement residual chlorine reaction amount, and the calibration standard residual chlorine reaction amount; a computing equation for computing a post-calibration residual chlorine reaction amount when the concentration is lower than the selected standard residual chlorine concentration based on the on-measurement residual chlorine reaction amount and the calibration factor when the concentration is lower than the selected standard residual chlorine concentration; and a computing equation for computing a post-calibration residual chlorine reaction amount when the concentration is equal to or higher than the selected standard residual chlorine concentration based on the on-measurement residual chlorine reaction amount and the calibration factor for when the concentration is equal to or higher than the selected standard residual chlorine concentration; and wherein the residual chlorine concentration computation section refers to the standard table stored in the residual chlorine concentration computation data storage section to specify a pre-calibration selected standard residual chlorine reaction amount, substitutes the specified pre-calibration selected standard residual chlorine reaction amount, the calibration standard residual chlorine reaction amount specified by the calibration factor computation section and the on-measurement residual chlorine reaction amount of the sample water into the computing equation for computing a post-calibration selected standard residual chlorine reaction amount that has been stored in the residual chlorine concentration computation data storage section to compute the post-calibration selected standard residual chlorine reaction amount, substitutes the on-measurement residual chlorine reaction amount of the sample water and the calibration factor for when the concentration is lower than the selected standard residual chlorine concentration into the computing equation for computing a post-calibration residual chlorine reaction amount when the concentration is lower than the selected standard residual chlorine concentration to compute the post-calibration residual chlorine reaction amount when the concentration is lower than the selected standard residual chlorine concentration, when the computed post-calibration selected standard residual chlorine reaction amount is higher than the on-measurement residual chlorine reaction amount of the sample water, substitutes the on-measurement residual chlorine reaction amount of the sample water and the calibration factor for when the concentration is equal to or higher than the selected standard residual chlorine concentration into the computing equation for computing a post-calibration residual chlorine reaction amount when the concentration is equal to or higher than the selected standard residual chlorine concentration to compute the post-calibration residual chlorine reaction amount when the concentration is equal to or higher than the selected standard residual chlorine concentration, and when the computed post-calibration selected standard residual chlorine reaction amount is lower than the on-measurement residual chlorine reaction amount of the sample water, refers to the standard table stored in the residual chlorine concentration computation data storage section to specify, as a post-calibration residual chlorine concentration, a residual chlorine concentration corresponding to the computed post-calibration residual chlorine reaction amount when the concentration is lower than the selected standard residual chlorine concentration or the computed post-calibration residual chlorine reaction amount when the concentration is equal to or higher than the selected standard residual chlorine concentration.

2. The residual chlorine meter of claim 1, further comprising a calibration factor computation data update control section;

wherein the detection section comprises a residual chlorine sensor, an amplifier, and an AD converter;

wherein the residual chlorine sensor is replaceable;

wherein the input section is for selecting a factor corresponding to a characteristic value that represents the post-replacement characteristic of the residual chlorine sensor; and wherein the calibration factor computation data update control section is for updating the standard table stored in the calibration factor computation data storage section by multiplying a residual chlorine reaction amount in the standard table by the factor corresponding to a characteristic value that represents the post-replacement characteristic of the residual chlorine sensor that has been input by the input section.

3. A residual chlorine meter comprising:

a detection section;

a calibration factor computation data storage section;

a calibration factor computation section;

a calibration factor storage section;

a residual chlorine concentration computation data storage section; and a residual chlorine concentration computation section;

wherein the detection section is for detecting a pre-calibration residual chlorine reaction amount and an on-measurement residual chlorine reaction amount of sample water;

wherein the calibration factor computation data storage section is for storing, in advance, a computing equation for computing a calibration factor for when the concentration is lower than a selected standard residual chlorine concentration based on the pre-calibration residual chlorine reaction amount and a predetermined calibration standard residual chlorine concentration, and a computing equation for computing a calibration factor for when the concentration is equal to or higher than the selected standard residual chlorine concentration based on the pre-calibration residual chlorine reaction amount and a predetermined pre-calibration selected standard residual chlorine reaction amount;

wherein the calibration factor computation section substitutes the pre-calibration residual chlorine reaction amount of the sample water into the computing equation for computing a calibration factor for when the concentration is lower than the selected standard residual chlorine concentration, and into the computing equation for computing a calibration factor for when the concentration is equal to or higher than the selected standard residual chlorine concentration, to compute the calibration factor for when the concentration is lower than the selected standard residual chlorine concentration and the calibration factor for when the concentration is equal to or higher than the selected standard residual chlorine concentration;

wherein the calibration factor storage section stores the calibration factor for when the concentration is lower than the selected standard residual chlorine concentration and the calibration factor for when the concentration is equal to or higher than the selected standard residual chlorine concentration that have been computed by the calibration factor computation section;

wherein the residual chlorine concentration computation data storage section is for storing, in advance, a computing equation for computing a post-calibration residual chlorine concentration based on the selected standard residual chlorine concentration that indicates a borderline at which the trend in the relationship between a residual chlorine concentration and a residual chlorine reaction amount changes prominently, a selected standard residual chlorine reaction amount which corresponds to the selected standard residual chlorine concentration, the on-measurement residual chlorine reaction amount and the calibration factor for when the concentration is lower than the selected standard residual chlorine concentration; and a computing equation for computing a post-calibration residual chlorine concentration when the concentration is equal to or higher than the selected standard residual chlorine concentration based on the on-measurement residual chlorine reaction amount, the calibration factor for when the concentration is equal to or higher than the selected standard residual chlorine concentration, and the selected standard residual chlorine concentration;

wherein the residual chlorine concentration computation section substitutes the on-measurement residual chlorine reaction amount of the sample water and the calibration factor for when the concentration is lower than the selected standard residual chlorine concentration into the computing equation for computing a post-calibration residual chlorine concentration when the concentration is lower than the selected standard residual chlorine concentration to compute the post-calibration residual chlorine concentration when the concentration is lower than the selected standard residual chlorine concentration; and wherein, when the selected standard residual chlorine reaction amount stored in the residual chlorine concentration computation data storage section is higher than the on-measurement residual chlorine reaction amount of the sample water, the residual chlorine concentration computation section substitutes the on-measurement residual chlorine reaction amount of the sample water and the calibration factor for when the concentration is equal to or higher than the selected standard residual chlorine concentration into the computing equation for computing a post-calibration residual chlorine concentration when the concentration is equal to or higher than the selected standard residual chlorine concentration, to compute the post-calibration residual chlorine concentration when the concentration is equal to or higher than the selected standard residual chlorine concentration when the selected standard residual chlorine reaction amount stored in the residual chlorine concentration computation data storage section is lower than the on-measurement residual chlorine reaction amount of the sample water.

* * * * *